United States Patent [19]

Milnamow

[11] 3,999,545
[45] Dec. 28, 1976

[54] DIAPER HAVING TAB FASTENER WITH ZONE COATED ADHESIVE

[75] Inventor: John P. Milnamow, North Barrington, Ill.

[73] Assignee: Johnson & Johnson, New Brunswick, N.J.

[22] Filed: Dec. 19, 1975

[21] Appl. No.: 642,286

[52] U.S. Cl. .............................. 128/284; 128/287
[51] Int. Cl.² .................... A61F 13/16; A41B 13/02
[58] Field of Search .......................... 128/284, 287

[56] References Cited
UNITED STATES PATENTS

| 3,646,937 | 3/1972 | Gellert | 128/287 |
|---|---|---|---|
| 3,848,594 | 11/1974 | Buell | 128/284 |
| 3,874,386 | 4/1975 | Kozak | 128/287 |
| 3,893,460 | 7/1975 | Karami | 128/287 |
| 3,952,744 | 4/1976 | Aldinger | 128/287 |

*Primary Examiner*—Aldrich F. Medbery

[57] ABSTRACT

A disposable diaper having a facing sheet defining a diaper inside surface for direction toward an infant and a backing sheet defining a diaper outside surface is provided with adhesive tabs comprising a backing web and a face web. The backing web is folded over to form first and second anchoring legs which are attached to a marginal portion of the diaper received therebetween. The face web has a fixed end permanently attached to the diaper outside surface inwardly of the backing web, an uncoated central region, and a free working end provided with a layer of adhesive. The free end is movable from a folded-over storage position, in which the adhesive layer is releasably attached to a release means provided on the outer surface of the first anchoring leg, to a working position in which the adhesive layer is available to secure the diaper about an infant. The release means preferably extends along the outer face of the entire backing web.

8 Claims, 4 Drawing Figures

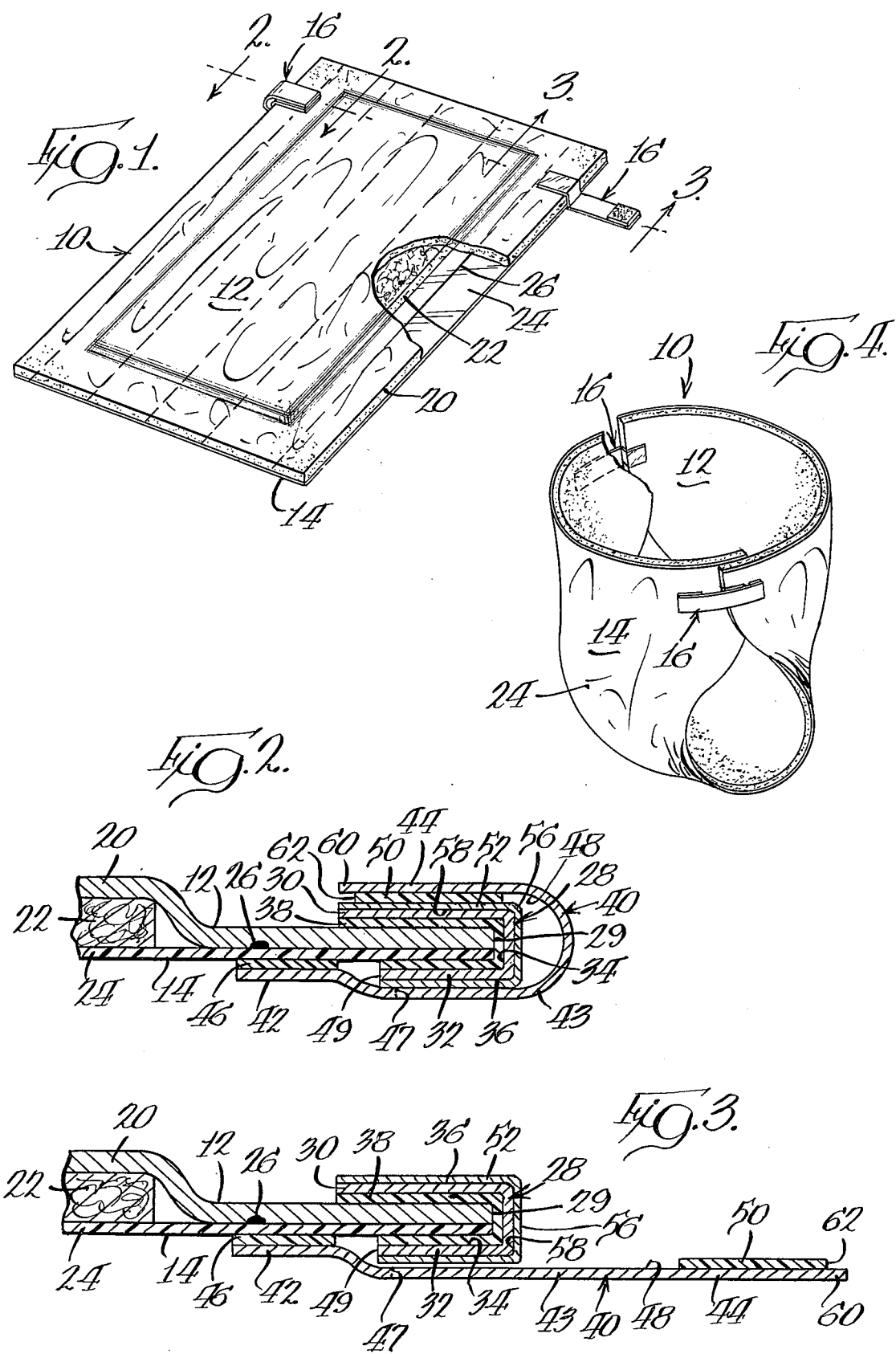

DIAPER HAVING TAB FASTENER WITH ZONE COATED ADHESIVE

BACKGROUND OF THE INVENTION

This invention relates to disposable diapers. More particularly, this invention relates to disposable diapers adapted to be secured in place by adhesive tabs.

Disposable diapers provide substantial advantages in convenience over diapers intended to be laundered and reused, particularly when they are used away from home. In recent years, many different disposable diapers have been proposed and some have been successful in the marketplace. Typical disposable diaper structures comprise a moisture-retaining layer of high liquid-holding capacity and a moisture-impervious backing sheet therefor, generally made of a plastic film such as polyethylene film or the like. Typical disposable diaper structures are shown in U.S. Pat. No. 3,612,055 to Mesek et al. and in U.S. Pat. No. Re. 26,151 to Duncan et al.

As may be seen from the above-cited patents, it is desirable to obviate the problems that are inherent in closure systems which utilize extraneous fasteners such as safety pins, snaps and zippers. To this end adhesive closure systems have presented acceptable solutions.

In order to protect the adhesive surfaces of the tape tabs, usually a cover strip having a release surface is applied over these adhesive surfaces for subsequent removal when the diaper is about to be used. However, such tabs usually project beyond the confines of the diaper to a considerable extent and interfere with the efficient manufacture and packaging of the diaper.

U.S. Pat. No. 3,616,114 to Hamaguchi et al. discloses an adhesive sealing tape which can be used for releasably interconnecting parts of a diaper or other container. The fixed end of a main tape portion is attached to one side of a first container part. A reinforcing tape portion is provided with a turned up end which is attached to the undersurface of the midregion of the main tape portion, and a part of the reinforcing tape portion is attached to the opposite side of the first container part. The free end of the main tape portion is adapted for attachment to a second container part which is to be secured to the first container part. Thus, the Hamaguchi et al. patent requires two specially interconnected tape portions. Moreover, the turned up end of the reinforcing tape portion causes the folded configuration of the sealing tape to be somewhat bulky.

The adhesive fastener disclosed in U.S. Pat. No. 3,833,456 to Reed et al. can also be attached to both the front and back surfaces of a diaper to provide for force distribution over both surfaces. This particular fastener comprises two coextensive webs with each web having an adhesive coating extending along substantially all of one face. The lower or base web also has a release coating on one end portion of its opposite face so that a portion of the adhesive coating on the upper web is releasably secured thereto while the rest of the adhesive coating on the upper web bonds the two webs together. Since two substantially co-extensive webs are present, the fastener is bulky in the folded configuration, and is relatively expensive to manufacture.

A similar tape fastener is shown in U.S. Pat. No. 3,848,594 to Buell wherein the tape fastener is also attached to both the front and back surfaces of the diaper while having a securing portion attached to an adjacent section of the diaper, but has the disadvantage in that each tape fastener is comprised of two or more separate tape segments which are joined together so as to produce a common area of joinder for both fastener anchoring legs and the fastener securing portion and thereby adding complexities and expense to the manufacturing process, as well as requiring careful positioning during diaper manufacture.

The prior art patents require that the tape fastener have one end for attachment to an opposite corner of the diaper and an oposite end directly attached to both faces of the diaper in order to distribute stresses through the diaper.

SUMMARY OF THE INVENTION

According to the present invention, stresses imposed on the tab are more widely distributed throughout the diaper without attaching one end of the tab to both faces of the diaper. Each tape tab which is used to secure the diaper about an infant includes a backing web which is folded over to define two anchoring legs which are permanently attached to a marginal portion of the diaper received therebetween. A face web has a fixed end permanently attached to the diaper outside surface inwardly of the backing web, an integral, uncoated non-tacky central region, and a free working end provided with a layer of adhesive. The free end is movable from a folded-over storage position, in which the adhesive layer is releasably attached to a release means provided on the outer surface of the first anchoring leg, to a working position in which the adhesive layer is available to secure the diaper about an infant.

The folded-over backing web reinforces and strengthens the marginal edge region of the diaper. By attaching the fixed end of the face web to the diaper outside surface away from the marginal edge of the diaper, inwardly of the attachment of the backing web to the diaper, stresses imposed on the backing sheet as the diaper moves about are more widely distributed through the backing sheet to thereby improve the distribution of stresses.

The release means preferably extends along the entire outer face of the backing web so that a user who is fastening the diaper about an infant can remove the free end of the face web from the release surface on the first anchoring leg and temporarily park the free end in an intermediate position on the release surface on the second anchoring leg of the backing web while the diaper is adjusted about the infant.

The tape tab fasteners of the present invention remain flat against the diaper when in the folded configuration and will not interfere with the diaper manufacturing machinery and the subsequent folding and packaging operations. Additional features of this invention include a tape tab which is relatively easy to affix to the diaper, and which provides good bond strength. The uncoated central region of the face web permits tearing or severing of the tab to facilitate removal of the tab from an infant, and also provides more flexibility in the central region of the face web to absorb and dissipate stress which is imposed on the tab as the infant moves about, thereby minimizing the load on the free end of the face web.

Brief Description of the Drawings

FIG. 1 is a perspective view, partially broken away to show interior detail, of an open unfolded diaper in accordance with the present invention;

FIG. 2 is an enlarged fragmentary cross-sectional view of the diaper of FIG. 1 taken along plane 2—2;

FIG. 3 is an enlarged fragmentary cross-sectional view of the diaper of FIG. 1 taken along plane 3—3; and FIG. 4 is a perspective view of the diaper of FIG. 1 in a configuration assumed by the diaper when placed about an infant.

Description of the Preferred Embodiments

Disposable diaper 10, illustrated in FIGS. 1 and 4, is of substantially quadrilateral configuration and presents inside surface 12 for direction toward an infant and outside surface 14 for direction away from the infant. Adhesive tab fastener means such as tabs 16 are attached to diaper 10 for securing diaper 10 about an infant. As described in greater detail below, tabs 16 are movable from a folded-over storage position illustrated in FIG. 2 to a working position which is illustrated in FIG. 3.

Referring to FIGS. 1-3, diaper 10 comprises moisture-pervious facing sheet 20, defining diaper inside surface 12 and overlying moisture-retaining absorbent pad 22, and backing sheet 24 which is made of a moisture-impervious material and defines diaper outside surface 14. Absorbent pad 22 is somewhat smaller than backing sheet 24 and is centrally disposed thereon; however, absorbent pad 22 can be made coextensive with backing sheet 24, if desired. Facing sheet 20 is substantially coextensive with backing sheet 24. Both facing sheet 20 and pad 22 can be anchored to the backing sheet 24 by means of adhesive beads 26, glue spots or in any other convenient manner. For example, if backing sheet 24 is made of a thermoplastic material, facing sheet 20 and pad 22 can be attached thereto by heat bonding.

As illustrated in FIGS. 2 and 3, adhesive tab 16 comprises backing web 28 which is folded over about longitudinal edge 29 of diaper 10 so as to define first and second anchoring legs 30, 32 each having an inner face 34 and an outer face 36. Anchoring legs 30, 32 perferably are about equal in width and are in a substantially juxtaposed relationship to one another. First anchoring leg 30 may be slightly longer than second anchoring leg 32, as discussed below. Anchoring legs 30, 32 receive a marginal portion of the diaper therebetween, and are provided with an adhesive coating which may comprise coated zones or a continuous adhesive coating 38 on the inner face 34 thereof. First anchoring leg 30 is permanently attached to facing sheet 20 and second anchoring leg 32 is permanently attached to backing sheet 24 by means of adhesive coating 38. Adhesive coating 38 can be a pressure-sensitive adhesive composition, a heat-activated or solvent-activated adhesive composition, or the like.

Tab 16 further includes face web 40 having web extremities zone-coated with an adhesive and having fixed end 42, non-adhesive integral central region 43 and free working end 44. Fixed end 42 of face web 40 is permanently attached to diaper outside surface 14 by means of adhesive coatig 46 on inside surface 14 by end 42. Folded-over backing web 28 reinforces the marginal edge region of diaper 10, and fixed end 42 of face web 40 is attached to diaper outside surface 14 inwardly of inner edge 49 of second anchoring leg 32. By attaching fixed end 42 away from the marginal edge of the diaper, stresses imposed on backing sheet 24 as the infant moves about can be more widely distributed through the diaper. As shown in FIGS. 2 and 3, fixed end 42 is preferably attached to diaper outside surface 14 at a location inwardly spaced from inwardly positioned edge 49 of second anchoring leg 32; however, if desired, fixed end 42 can be attached adjacent to but spaced from edge 49 of second anchoring leg 32 so that fixed end 42 can shift somewhat relative to backing web 28 as the region of backing sheet 24 surrounding fixed end 42 is extended when tab 16 is subjected to tension. Also, preferably second anchoring leg 32 is slightly shorter than first anchoring leg 30 so that tab 16 does not have to be excessively long and fixed end 42 can be attached to diaper outside surface 14 reasonably close to the marginal edge of the diaper.

Pressure-sensitive adhesive coating 50 is provided on the free working end portion of inside face 48, faces in the same direction as diaper inside surface 12 when tab 16 is in the working position, and provides a securement means which can be moved from the closed, storage position of FIG. 2 to the open working position of FIG. 3 for fastening the diaper about an infant. Uncoated central region 43 permits convenient tearing or severing of the tab fastener once the diaper has been placed about the infant. If desired, line of weakening 47 can be provided in uncoated, non-tacky central region 43 of face web 40 to facilitate tearing of the tab fastener upon removal of the diaper from the infant. Since central region 43 of face web 40 is uncoated, central region 43 has somewhat greater flexibility than the tab end portions and has the capacity to absorb and distribute stresses imposed on face web 40 as the infant moves about. The imposed load on free end 44 of face web 40 is thereby minimized.

Release means 52 is provided on outer face 36 of first anchoring leg 30 and provides a release facing substantially in the same direction as diaper inside surface 12. When tab 16 is in the storage position of FIG. 2, adhesive coating 50 on free end 44 of face web 40 is releasably adhered to release means 52 which is substantially coextensive with adhesive coating 50. Release means 52 preferably extends along outer face 36 of the entire backing web 28 so that a user who is about to fasten diaper 10 about an infant can remove free end 44 from its storage engagement with first anchoring leg 30 and, if desired, temporarily place free end 44 in an intermediate position in which free end 44 is releasably secured to second anchoring leg 32 while diaper 10 is positioned.

Release means 52 may comprise a ribbon segment or release strip carried by backing web 28 and provided with a release coated face 56 which provides the release region, and an adhesive coating on opposite face 58 by means of which the release strip is anchored to backing web 28. Release coated face 56 faces in the same direction as diaper inside surface 12 along first anchoring leg 30. Alternatively, release means 52 may comprise a release coating, such as a silicone release compound, or the like, on the outer face 36 of backing web 28 and which is substantially coextensive with adhesive coating 50 on free end 44 of face web 40 when tab 16 is folded to the storage position.

It is desirable to provide a gripping means to facilitate grasping tab 16 to separate adhesive coating 50 on free end 44 of face web 20 from release means 52 preparatory to fastening the diaper about an infant. As shown in FIG. 2, free end 44 can include projecting portion 60 which extends inwardly on diaper 10 beyond outermost margin or end 62 of adhesive coating 50. The outwardly extending segment 60 provides a gripping means for separating adhesive coating 50 on face web 40 from release means 52.

Adhesive tabs suitable for the purposes of the present invention can be made from a wide variety of materials, provided that such materials are sufficiently flexible. Preferred materials for this purpose are polyalkylene webs such as polyethylene sheet, polypropylene sheet, and the like. Particularly preferred are webs which are oriented along the narrow dimension of the tab or webs which have filament reinforcements therein.

The pressure-sensitive adhesive layers such as adhesive coating 50 are provided by applying a coating of a pressure-sensitive adhesive composition known in the art to the appropriate surface of tab 16. The applied adhesive shall have good tack, good cohesive strength, good resistance to moisture and good resistance to aging. Illustrative of such adhesive compositions are mixtures of natural or synthetic rubber, zinc oxide, and various resins, also latices of natural or synthetic rubber, or water dispersions of acrylic tacky polymers or copolymers, and the like.

Anchored release strips can be made from smooth plastic film having a relatively non-adhering surface, from paper coated with a silicone release compound, or from similar release materials. A number of appropriate release coatings may be used with the present invention. Examples of such coatings are disclosed in U.S. Pat. No. 2,822,290 to Webber; U.S. Pat. No. 2,880,862 to Sermattei; and U.S. Pat. No. 2,985,554 to Dickard.

Several different types of facing materials may be used for diaper facing sheet 20. For example, facing sheet 20 may be made up of a mixture of fibers consisting predominantly of inexpensive short cellulosic fibers such as wood pulp fibers or cotton linters, in amounts of about 75% to about 98%, the balance being textile length fibers such as rayon as described in U.S. Pat. No. 3,663,348 to Liloia et al.

Facing sheet materials suitable for use in this invention can have fabric weights in the range of about 1 to 5 oz./yd$^2$ and densities of less than 0.15 g./cc., generally in the range between 0.05 and 0.1 g./cc. The dry strength of the facing sheet for a fabric having a weight of about 1.5 oz./yd$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 20 may also be made of an apertured, non-woven fabric which is formed, for example, in accordance with the teachings of commonly assigned U.S. Pat. Nos. 2,862,251, 3,081,514 and 3,081,515. Briefly, such fabrics are foraminous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd$^2$.

In addition, facing sheet 20 can be formed of a non-apertured material, such as a nonwoven isotropic web, or the like. In all of the aforementioned facing materials, the material should be relatively hydrophobic so as to retard wicking within the facing layer. Also suitable are porous polymeric sheet materials such as polyalkylene webs having a fibrous surface, and the like.

Highly moisture-absorbent fibrous pad or batt 22, which usually is substantially rectangular in shape but smaller than the facing sheet and the backing sheet, can be formed in accordance with the teachings of U.S. Pat. No. 3,612,055 to Mesek et al. If desired, a highly moisture-absorbent layer can be provided substantially coextensive with backing sheet 24 and facing sheet 20.

A suitable backing sheet material for the diapers embodying the present invention can be an opaque polyethylene web about 0.001 inch thick. Another suitable material for this purpose is a polyethylene terephthalate web having a thickness of about 0.0005 inch. Typical disposable diapers which can be fitted with tab-type adhesive fasteners described hereinabove are shown in U.S. Pat. No. 3,612,055 to Messek et al. and in U.S. Pat. No. 3,683,916 to Mesek et al. Other suitable disposable diaper structures which can be improved by the present tab-type fasteners are shown in U.S. Pat. No. Re. 26,151 to Duncan et al.

In use, a diaper equipped with the adhesive fasteners of the present invention is applied to the infant by laying out the diaper on a suitable flat surface and placing the infant thereon so that the waist-underlying end of the diaper is that having the tab fastener means. The other end of the diaper then extends downwardly between the infant's legs. Next, the downwardly extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive fasteners are then prepared for use by pulling free end 44 of face web 40 away from its temporary engagement with release means 52, exposing adhesive coating 50 which was releasably adhered to release means 52. The tabs are then used to secure the diaper in the desired position by simply urging the pressure-sensitive adhesive surfaces in contact with the adjacent outer surface of the diaper. The applied diaper assumes the configuration illustrated in FIG. 4.

The foregoing description and the drawing are illustrative but are not to be taken as limiting. Still other variations and modifications are possible without departing from the spirit and scope of the present invention.

I claim:

1. A disposable diaper having a facing sheet defining a diaper inside surface for direction toward an infant, a moisture-impervious backing sheet substantially coextensive with said facing sheet and defining a diaper outside surface, an absorbent panel positioned between said facing sheet and said backing sheet, and an adhesive tab fastener means which comprises:

a backing web folded over to form first and second anchoring legs each having an inner face and an outer face, and receiving a marginal portion of the diaper therebetween, said inner face of said legs being provided with an adhesive coating by means of which said legs are permanently attached to said marginal portion, said first leg being attached to said diaper inside surface, and said second leg being attached to said diaper outside surface;

release means on said outer face of said backing web and extending along at least a portion of said first leg and providing a release region facing substantially in the same direction as said diaper inside surface; and a face web having a fixed end permanently attached to said diaper outside surface inwardly of said backing web, an integral non-tacky central region and a free working end extending outwardly across said second leg and provided with a layer of pressure-sensitive adhesive facing in the same direction as said diaper inside surface when said tab fastener means is in a working position;

said free end being movable from a folded-over storage position in which said free end is releasably adhered to said release region to said working position in which said free end is available for securing said diaper about an infant.

2. The disposable diaper as defined in claim 1 wherein said release means extends along said outer face of the entire backing web.

3. The disposable diaper as defined in claim 1 wherein said fixed end is attached to said diaper outside surface at a location adjacent to said second anchoring leg.

4. The disposable diaper as defined in claim 1 wherein said fixed end is attached to said diaper outside surface at a location spaced from said second anchoring leg.

5. The disposable diaper as defined in claim 1 wherein said adhesive coating on said inner face of said anchoring legs comprises a continuous adhesive coating on one face of said backing web.

6. The disposable diaper as defined in claim 1 wherein said release means is a release coating on said outer face of said backing web.

7. The disposable diaper as defined in claim 6 wherein said release coating comprises a silicone release compound.

8. The disposable diaper as defined in claim 1 wherein said release means comprises a ribbon segment which has one face adhesively affixed to the outer face of said backing web and an opposite face having a release coating.

* * * * *